United States Patent [19]

Kretschmann et al.

[11] Patent Number: 4,973,686
[45] Date of Patent: Nov. 27, 1990

[54] PROCESS FOR THE SULFONATION AND/OR SULFATIZATION OF ORGANIC COMPONENTS WITH SO₃ IN AN ORGANIC REACTION MEDIUM

[75] Inventors: Josef Kretschmann, Langenfeld; Franz-Josef Carduck, Haan; Willi Wuest, Ratingen; Hubert Harth, Hilden; Dirk Springer, Haan, all of Fed. Rep. of Germany

[73] Assignee: Henkel Kommanditgesellschaft auf Aktien, Duesseldorf-Holthausen, Fed. Rep. of Germany

[21] Appl. No.: 240,789

[22] Filed: Sep. 2, 1988

[30] Foreign Application Priority Data

Sep. 3, 1987 [DE] Fed. Rep. of Germany ....... 3729416

[51] Int. Cl.⁵ .................. C07H 13/00; C07H 1/00; C08B 37/00; C07C 303/00
[52] U.S. Cl. .................. 536/118; 536/124; 536/119; 536/122; 260/400; 562/123; 562/98; 562/95
[58] Field of Search .......... 536/124, 118, 119, 122; 260/400; 562/123, 98, 95; 558/41

[56] References Cited

U.S. PATENT DOCUMENTS

| | | | |
|---|---|---|---|
| 2,413,199 | 12/1946 | Taylor | 562/123 |
| 3,097,218 | 7/1963 | Kooijman et al. | 260/400 |
| 3,864,375 | 2/1975 | Kitano et al. | 260/459 |
| 4,579,687 | 4/1986 | Sekiguchi et al. | 260/400 |

FOREIGN PATENT DOCUMENTS 2320933 11/1973 Fed. Rep. of Germany .

OTHER PUBLICATIONS

Chemical Reviews, vol. 62, 1962 pp. 549–580.
Encyclopedia of Chemical Technology, 3rd Edition, vol. 22, pp. 1–45.

Primary Examiner—Ronald W. Griffin
Assistant Examiner—Everett White
Attorney, Agent, or Firm—Ernest G. Szoke; Wayne C. Jaeschke; Daniel S. Ortiz

[57] ABSTRACT

The invention relates to the use of selected carboxylic acid esters which are liquid under reaction conditions and correspond to general formula (I)

$$X\text{---}COOR^1 \qquad \text{(I)}$$

in which $R^1$ is an alkyl radical unbranched in the α-position and X is hydrogen or a group corresponding to general formula (II)

$$R^3\text{---}\underset{\underset{R^4}{|}}{\overset{\overset{R^2}{|}}{C}}\text{---} \qquad \text{(II)}$$

in which $R^2$, $R^3$ and $R^4$ represent fluorine and/or chlorine and one of these substituents may also be hydrogen or one or two of these substituents may also be lower alkyl, as reaction medium for the sulfonation and/or sulfatization or organic components with SO₃ to light-colored reaction products.

19 Claims, No Drawings

PROCESS FOR THE SULFONATION AND/OR SULFATIZATION OF ORGANIC COMPONENTS WITH SO3 IN AN ORGANIC REACTION MEDIUM

BACKGROUND OF THE INVENTION

1. Field of Invention

In practice, the sulfonation of organic compounds by reaction with sulfur trioxide ($SO_3$) comprises in particular reactions of the sulfonation and/or sulfatization type, of which the reaction scheme is known and may be re-presented as follows:

sulfonation: $R-H + SO_3 \rightarrow RSO_3H$ sulfatization: $R-OH + SO_3 \rightarrow ROSO_3H$ Reactions of this type are distinguished by very fast kinetics, but are also burdened by the release of considerable heat of reaction which can amount, for example, to between 100 and 180 kJ/mol. In reaction systems of comparatively high viscosity, this presents heat dissipation problems, so that local overreactions, overheating, carbonization, dehydration and/or polymerization can often be initiated. Oxidation reactions initiate discoloration which adversely affects the quality of the reaction products, so that the sulfonation and/or sulfatization products generally have to be bleached and purified.

2. Statement of Related Art

Among the technical embodiments of these reactions, a gasliquid reaction with gaseous sulfur trioxide, diluted in an inert gas, on thin liquid films occupies a prominent position Although, in many cases, organic compounds can be sulfonated and/or sulfatized under relatively mild reaction conditions by using chlorosulfonic acid, sulfuric acid or oleum instead of sulfur trioxide, the hydrogen chloride given off or the sulfuric acid formed have to be separated with considerable effort. Finally, many particularly sensitive substrates cannot be satisfactorily sulfonated and/or sulfatized with conventional agents.

To reduce, if not completely eliminate, these disadvantages during the sulfonation and/or sulfatization reaction, attempts have been made to reduce the extreme reactivity of sulfur trioxide by addition of solvents. The use of solvents provides for better distribution and admixture of the reactants and, easier heat dissipation, for isothermal conduct of the reaction (see for example E. E. Gilbert in "Chemical Reviews" 62, 549 to 580 (1962); Kirk-Othmer in "Encyclopedia of Chemical Technology" 22, 1 to 45 (1983).

Sulfur dioxide or halogenated hydrocarbons for example have been proposed as solvents. The use of liquid sulfur dioxide, which is toxic and highly corrosive, involves handling problems and, in addition, is applicable only to reactions involving relatively non-sensitive aromatics. The other solvents proposed for sulfur trioxide, such as low-boiling halogenated hydrocarbons, paraffins, cyclic ethers and also tertiary amines, can also give rise to considerable difficulties. Solvents of this type can produce violent reactions with $SO_3$. On completion of sulfonation and/or sulfatization, secondary reaction products formed during preparation of the sulfonating and/or sulfatizing agent have to be separated generally with difficulty in addition to the solvent.

The object of the present invention is to provide a safe and comparatively non-sensitive reaction medium, present in the liquid phase under the reaction conditions for the sulfonation of organic components with $SO_3$, which provides for improved monitoring and control of the reaction to such an extent that unwanted secondary reactions can be substantially or even completely eliminated. Accordingly, the invention makes known sulfonation reactions of the type mentioned easier to control. The process of the invention makes it possible to carry-out specific sulfonation reactions on highly sensitive substrates which, hitherto, could not be considered for sulfonation with $SO_3$.

BRIEF DESCRIPTION OF INVENTION

According to the invention, applicants have unexpectedly discovered that certain selected carboxylic acid esters are particularly suitable as a reaction-moderating reaction medium and/or diluent for sulfonation or sulfatization using $SO_3$.

Carboxylic acid esters are active reactants known for sulfonation reactions with $SO_3$. In practice, this chemical reaction is widely used in the production of α-sulfonated fatty acid esters or corresponding o-sulfonated fatty acids and/or salts thereof. This reaction has acquired practical significance in the production of surface-active components from the groups consisting of ester sulfonate salts and/or the salts of α-sulfofatty acids. The characteristic element of all sulfonation reactions of the type under discussion here is the introduction of the sulfo acid group in the α-position of the carboxylic acid.

The invention proposes using, as a process-controlling reaction medium, carboxylic acids which are not capable of sulfonation in the α-position and which, in addition, do not contain any structural elements that could give rise to unwanted secondary reactions particularly with $SO_3$.

In a first embodiment, therefore, the present invention relates to the use of selected carboxylic acid esters which are liquid under reaction conditions and which correspond to the following formula $$X-COOR^1 \qquad (I)$$

in which $R^1$ is an alkyl radical unbranched in the α-position and X is hydrogen or a group corresponding to the formula $$\begin{array}{c} R^2 \\ | \\ -C-R^3 \\ | \\ R^4 \end{array} \qquad (II)$$

in which $R^2$, $R^3$ and $R^4$ independently represent fluorine or chlorine and one of $R^2$, $R^3$, or $R^4$ can also represent hydrogen or up to two of $R^2$, $R^3$ or $R^4$ can be lower alkyl, wherein at least one of $R^2$, $R^3$ and $R^4$ is fluorine or chlorine, as reaction medium for the sulfonation and/or sulfatization of organic compositions with $SO_3$ to light-colored reaction products.

The present invention also comprises a process for the production of light-colored reaction products in the sulfonation and/or sulfatization of organic components with $SO_3$ in the presence of diluents, characterized in that the carboxylic acid esters, which are liquid under reaction conditions, and correspond to general formula I, in which X and $R^1$ are as defined, are used as diluents and, on completion of the reaction, the carboxylic acid esters are separated off from the sulfonation or sulfatization products preferably by distillation and/or liquid extraction.

DETAILED DESCRIPTION OF THE INVENTION

Other than in the operating examples, or where otherwise indicated, all numbers expressing quantities of ingredients or reaction conditions used herein are to be understood as modified in all instances by the term "about".

The carboxylic acid esters useful in the practice of the invention, correspond to general formula I. The esters are all distinguished by the fact that they are not accessible to α-sulfonation used for production of α-sulfocarboxylic acid esters. They are generally good solvents for the organic compositions to be sulfonated or sulfatized where the organic composition show any solubility at all. It is not necessary that the organic compositions to be sulfonated or sulfatized be soluble in the ester. The reaction of finely disperse solids and suspensions of insoluble organic reactants in the carboxylic acid esters selected in accordance with the invention also falls within the scope of the invention.

The ester-based reaction medium is also capable of taking up $SO_3$, in molecularly disperse solution, and delivering it in this form to the controlled reaction.

It can be of advantage, particularly to facilitate separation of the ester used as reaction medium, to select carboxylic acid esters of the type mentioned from the point of view of their boiling characteristics. Preferred reaction media corresponding to general formula I are esters having boiling points at normal pressure of up to about 250° C. and preferably of up to about 170° C. Carboxylic acid esters such as these, corresponding to general formula I, may readily be separated by distillation on completion of the sulfonation process.

However, the boiling characteristic of the carboxylic acid ester to be selected for the particular application can have an even greater significance. Thus, the maximum internal temperature of the reaction mixture can be determined by selecting the boiling temperature of the reaction medium of the invention under the process conditions. By selecting a suitable ester-forming acid composition and the associated alcohol composition, it is possible to predetermine the boiling characteristic of the ester and, the maximum temperature under the reaction conditions. Excess heat of reaction from the reaction taking place in the reaction zone (sulfonation and/or sulfatization) leads directly to partial evaporation of the reaction medium and, hence, to safer temperature control enabling predetermined maximum temperatures to be maintained. Surprisingly, this is a particularly simple method of producing light-colored products from otherwise temperature-sensitive reactants.

The substituent X in the selected carboxylic acid esters corresponding to the formula I may represent hydrogen Formic acid esters of this type are thus generally useful. There is no α-carbon atom in the carboxylic acid group, so that the reaction possibility is eliminated. On the alcohol side of the ester, it is merely important to ensure that there are no unwanted ester decomposition reactions under the effect of $SO_3$. Accordingly, the teaching according to the invention requires the exclusion of a branch in the α-position for the alcohol radical $R^1$. For the rest, these alkyl radicals may be linear or branched. The chain length of this alcohol radical determines the boiling point of the ester. The preferred upper boiling limits mentioned above for the reaction medium according to the invention should be taken into account here. $R^1$ is preferably a $C_1$–$C_8$ alkyl radical, more especially containing no more than 6 carbon atoms. The methyl, ethyl, propyl and/or butyl esters are particularly useful. This applies not only to the formic acid esters, but also to the other esters suitable for use in accordance with the invention, in which X is a group corresponding to general formula II.

Esters where X is a group of the formula II are derived from halogen-substituted carboxylic acids which may be of various different types but share the common characteristic that they do not lead to α-sulfonation with $SO_3$ under the reaction conditions applied in accordance with the invention. The alcohol component of the esters of this second group corresponds to the alcohol described in connection with the formic acid esters. The choice of lower alcohols particularly methyl and/or ethyl esters, provides for easy separation of the reaction media by distillation on completion of the sulfonation.

Trifluoroacetic acid and trichloroacetic acid are preferred acid components for the ester of the reaction media useful in the invention. Trifluoroacetic acid esters have particularly low boiling points while trichloroacetic acid is a particularly inexpensive chemical, so that the use of its esters are particularly interesting on economic grounds.

One of the substituents $R^2$, $R^3$ and $R^4$, in general formula II, can be hydrogen. The two halogen atoms present at the same carbon preclude α-sulfonation as an unwanted secondary reaction. However, one or two of these substituents $R^2$, $R^3$ and $R^4$ may also be lower alkyl radicals. Lower alkyl radicals are alkyl radicals containing up to 6 carbon atoms and preferably up to 3 carbon atoms. Adequate resistance to attack on the α-carbon atom by $SO_3$ is possessed by these compounds. However, at least one of $R^2$, $R^3$ or $R^4$ must be chlorine or fluorine.

The sulfonation and/or sulfatization reactions moderated in accordance with the invention, using selected carboxylic acid esters, may be carried out in various ways. It is possible to use $SO_3$ and/or the organic compositions to be reacted in at least partly premixed form with carboxylic acid esters of the formula I in the reaction zone. In one embodiment, solutions of the reactants in the carboxylic acid esters formula I are introduced into the reaction zone where they are mixed with one another under temperature control. Both the organic composition to be reacted and also the $SO_3$ or the $SO_3$-yielding composition can be used in admixture with the reaction medium used in accordance with the invention.

In practical application of this process, which is particularly suitable for batch operation, it will generally be preferred to introduce the organic component to be sulfonated together with part of the carboxylic acid ester used as the reaction medium into the reaction zone and then to introduce $SO_3$, preferably also dissolved in such reaction medium—into the reaction zone at a rate commensurate with the rate at which the heat of reaction generated can be controlled.

In another embodiment of the process of the invention, it is possible to improve the mixed-phase reaction where it is carried out continuously. In the mixed-phase reaction, the organic composition to be sulfonated is exposed in a thin layer liquid phase to an $SO_3$-containing gas phase. In this case, it is possible, in accordance with the invention, to moderate the reaction by initially introducing a solution of the organic composition to be sulfonated as a liquid phase and contacting it in a thin layer with an SO₃-containing gas stream either co-currently of countercurrently. The gas phase used may either be $SO_3$ as or $SO_3$ in admixture with an inert gas, such as nitrogen, or with air.

The carboxylic acid esters useful in the present invention, which cannot be sulfonated in the α-position, may be mixed in any ratio with sulfur trioxide and/or the organic compositions to be sulfonated. They form homogeneous solutions with sulfur trioxide. The $SO_3$ content of the solutions used, in accordance with the invention, depends on the properties of the organic compounds to be sulfonated and/or sulfatized. The more sensitive the organic substrates are to oxidation the lower the concentration of $SO_3$ in the solutions used must be. However, the concentration of $SO_3$ in the solutions will normally be from 10 to 60% by weight and more especially from 20 to 40% by weight. In some cases, it can be of advantage to use lower or even higher $SO_3$ concentrations.

The temperature in the reaction zone generally does not exceed about 100° C. The reaction is preferably carried out at temperatures of about 80° C. Particularly suitable reaction temperatures are temperatures of up to 60° C. for example in the range from 0° to 40° C. By selecting suitable esters of the invention, it is also possible, to carry out the reaction at temperatures below 0° C., for example in the range from −25° to +20° C. It is clear that this provides for particularly safe control of the process, thus allowing access to sulfonation and/or sulfatization reactions hitherto considered not possible.

The required reaction temperatures may be maintained or established by dissipation of the heat of reaction by cooling or, as already mentioned, by partial evaporation of the reaction medium according to the invention. A particularly simple indicator for unwanted secondary reactions is the color of the reaction mixture. Color is generally indicative of the extent of unwanted secondary reactions. According to the invention, it is possible to carryout even the most critical reaction to provide colorless or, at most, very faintly colored reaction products which, if desired, may be subsequently purified without difficulty.

The reaction medium according to the invention, based on carboxylic acid esters, may be removed not only by distillation, but in many cases also by selective extraction. Carboxylic acid esters of the defined type are comparatively hydrophobic constituents while the sulfonation and/or sulfatization products required as the reaction product are generally distinguished by a pronounced hydrophilic character. These differences may be used for extractive separation. In addition, the improved separation between reaction product and reaction medium, according to the invention, may be additionally influenced, for example by salt formation from the sulfonation products, for example by formation of the corresponding sodium salts.

The process according to the invention may be used within the broad context of the known sulfonation and/or sulfatization reaction of organic compositions and, in particular, may be used with a particular advantage anywhere where importance is attributed to defined reactions substantially free from unwanted secondary reactions.

In addition, however, the use of the reaction medium according to the invention, enables basically labile organic components to be subjected to controlled sulfonation and/or sulfatization which could not be carried out by processes which were hitherto available.

EXAMPLES

Example 1

2.98 g (27.3 mmol) sulfur trioxide were dissolved in 7.5 g trifluoroacetic acid methyl ester and the resulting solution added dropwise with stirring to a solution of 5.70 g (36.0 mmol) 1-decanol in 17.1 g trifluoroacetic acid methyl ester, the temperature being kept at around 30° C. by evaporation of the solvent. The solvent was then distilled off on a water bath at 55° C. and the residue neutralized with sodium hydroxide.

The yield of sodium decyl sulfate was determined in accordance with DIN/ISO 2271 and amounted to 9.36 g (100%).

Example 2

65.2 g (0.82 mol) sulfur trioxide were dissolved in 175 g trichloroacetic acid methyl ester and the resulting solution added with stirring on an ice bath to a solution of 122.6 g 1-decanol (0.77 mol) in 368 g trichloroacetic acid methyl ester, the temperature being kept below 15° C. Trichloroacetic acid methyl ester was distilled off at 70° C.-0.1 torr and the residue neutralized with sodium hydroxide.

The yield of sodium decyl sulfate was determined in accordance with DIN/ISO 2271 and amounted to.871.2 g (93%).

Example 3

19.2 g (0.24 mol) sulfur trioxide were dissolved in 80 g dichloroacetic acid methyl ester and the resulting solution added dropwise with stirring to a solution of 37.2 g (0.20 mol) 1-dodecanol in 10 g dichloroacetic acid methyl ester in an ice bath, the temperature rose to 30° C. The solvent was then distilled off and the residue neutralized with sodium hydroxide.

The yield of sodium dodecyl sulfate was determined in accordance with DIN/ISO 2271 and amounted to 43 g (80%).

Example 4

9.0 g (0.11 mol) sulfur trioxide were dissolved in 10 g trifluoroacetic acid ethyl ester and the resulting solution added dropwise with stirring to a solution of 12.0 g (0.11 mol) m-xylene in 5 g trifluoroacetic acid methyl ester so that the temperature did not rise above 20° C. On completion of the addition, the mixture was heated under reflux for 15 minutes. 3,5-dimethyl benzenesulfonic acid crystallized out on cooling. 12.7 g (54%) colorless, hygroscopic flakes deliquescing rapidly in air were obtained. Another 4.6 g (20%) product were obtained by concentration of the mother liquor. For characterization, 2 g of the sulfonic acid were converted into the corresponding acid amide and a melting point of 137° C. was determined (literature: 137° C.).

Example 5

8.7 g (0.11 mol) sulfur trioxide were dissolved in 18.8 g trichloroacetic acid methyl ester and the resulting solution added dropwise with stirring to a solution of 26.1 g (0.11 mol) technical alkylbenzene (molecular weight 240) in 60.9 g trichloroacetic acid methyl ester. The temperature was maintained below 20° C. by external cooling. The solvent was distilled off in vacuo and the residue neutralized with sodium hydroxide.

The yield of sodium alkylbenzenesulfonate was determined in accordance with DIN/ISO 2271 and amounted to 35.5 g (96%).

Example 6

5 g (0.06 mol) sulfur trioxide were dissolved in 40 g butyl formate and the resulting solution added dropwise at 80° C. to a solution of 80 g technical $C_{10}$-$C_{14}$ fatty alcohol glucoside in 20 g butyl formate. After 10 minutes, the wax-like solid mass was freed from the solvent under reduced pressure and neutralized with sodium hydroxide. The reaction product was dried in a high vacuum and ground in a laboratory mill. 84 g of a light yellow, water-soluble product containing 2.3% organically bound sulfur were obtained.

Example 7

A mixture of 22 g (0.28 mol) sulfur trioxide and 150 g formic acid ethyl ester was added dropwise at about 22° C. to 263 g (0.28 mol) castor oil and left for 12 hours at about 22° C. The solvent was then distilled off and the residue neutralized with sodium hydroxide. The $SO_3Na$ content was determined in accordance with DIN/ISO 2271 and amounted to 5% by weight $SO_3$.

Example 8

1.5 g (19 mmol) sulfur trioxide were dissolved in 5 g trichloroacetic acid methyl ester and the resulting solution added dropwise with stirring to a solution of 20 g (21 mmol) castor oil in 40 g trichloroacetic acid methyl ester, the temperature being maintained below 20° C. by external cooling with an ice bath. The solvent was distilled off at 60° C./0.1 torr and the residue neutralized with sodium hydroxide. The $SO_3Na$ content was determined in accordance with DIN/ISO 2271 and amounted to 6.3% by weight $SO_3$.

We claim:

1. In a process wherein an organic composition is sulfonated or sulfatized by reaction with $SO_3$, to form a sulfonated or sulfatized product, wherein the organic composition and the $SO_3$ are reacted in the presence of a liquid reaction medium, the improvement which comprises: using as the liquid reaction medium at least one carboxylic acid ester of the formula $$X\text{—COOR}^1 \qquad (I)$$

wherein $R^1$ is an alkyl radical unbranched in the α-position and X is hydrogen or a group of the formula

$$(II)$$

wherein $R^2$, $R^3$ and $R^4$ independently represent fluorine or chlorine, one of $R^2$, $R^3$ and $R^4$ can be hydrogen or up to two of $R^2$, $R^3$ and $R^4$ can be lower alkyl wherein at least one of $R^2$, $R^3$ or $R^4$ is fluorine or chlorine.

2. A process of claim 1 wherein at least one of the $SO_3$ or the organic composition is premixed with the carboxylic acid ester (I) before reaction.

3. A process of claim 1 wherein a solution of $SO_3$ in the carboxylic acid ester (I) and a mixture of the organic composition and the carboxylic acid ester (I) are admixed in the reaction zone and reacted at a temperature not higher than about 80° C.

4. A process of claim 1 wherein a mixture of the organic composition and the carboxylic acid ester is contacted with gaseous $SO_3$.

5. A process of claim 1 wherein the carboxylic acid ester has a boiling point at normal pressure not higher than about 250° C.

6. A process of claim 5 wherein the boiling point at normal pressure is not higher than about 170° C.

7. A process of claim 1 wherein the reaction medium is separated from the sulfonated or sulfatized product by at least one of distillation or liquid extraction.

8. A process of claim 1 wherein the organic composition is reacted with the $SO_3$ at a temperature not higher than about 40° C.

9. A process of claim 8 wherein the reaction temperature is controlled by cooling.

10. A process of claim 8 wherein the temperature of reaction is controlled at least in part by evaporation of the reaction medium.

11. A process of claim 9 wherein gaseous $SO_3$ is contacted with a thin layer of a mixture of the organic composition and the carboxylic acid ester.

12. A process of claim 10 wherein gaseous $SO_3$ is contacted with a thin layer of a mixture of the organic composition and the carboxylic acid ester.

13. A process of claim 1 wherein the organic composition comprises at least one composition selected from the group consisting of fatty alcohol, alkyl benzene, alkyl glucoside and castor oil.

14. A process of claim 1 wherein the liquid reaction medium comprises at least one carboxylic acid ester of the formula

wherein $R^1$ is an alkyl radical unbranched in the alpha position and $R^2$, $R^3$ and $R^4$ are independently hydrogen, lower alkyl, fluorine or chlorine wherein at least one of $R^2$, $R^3$ and $R^4$ is fluorine or chlorine, not more than two of $R^2$, $R^3$ and $R^4$ are lower alkyl and wherein not more than one of $R^2$, $R^3$ and $R^4$ is hydrogen.

15. A process of claim 14 wherein the $SO_3$ is mixed with the carboxylic acid ester before contacting the organic composition.

16. A process of claim 14 wherein a mixture of the organic composition in the carboxylic acid ester is contacted with gaseous $SO_3$.

17. A process of claim 14 wherein the organic composition and $SO_3$ are reacted at a temperature not higher than about 40° C.

18. A process of claim 14 wherein the temperature of the reaction is controlled, at least in part, by evaporation of the reaction medium.

19. A process of claim 14 wherein the boiling point of the carboxylic acid ester at normal pressure is not higher than about 170° C.

* * * * *